United States Patent [19]

Measamer et al.

[11] Patent Number: 5,601,575
[45] Date of Patent: Feb. 11, 1997

[54] NEEDLE DRIVING DEVICE

[75] Inventors: John P. Measamer, Cincinnati; Robert F. Welch, Maineville; Brett Swensgard, Massillon, all of Ohio

[73] Assignee: Ethicon Endo-Surgery, Inc., Cincinnati, Ohio

[21] Appl. No.: 319,182

[22] Filed: Oct. 6, 1994

Related U.S. Application Data

[63] Continuation-in-part of Ser. No. 300,295, Sep. 2, 1994.
[51] Int. Cl.$^6$ ................................................. A61B 17/04
[52] U.S. Cl. ............................ 606/147; 606/144; 606/146
[58] Field of Search ................................ 606/147, 139, 606/144, 146

[56] References Cited

U.S. PATENT DOCUMENTS

| | | | |
|---|---|---|---|
| 1,266,456 | 5/1918 | Greeley | 606/147 |
| 3,120,847 | 2/1964 | Cavaness | 606/147 |
| 4,949,717 | 8/1990 | Shaw | 606/147 |
| 5,257,999 | 11/1993 | Slanetz | 606/147 |
| 5,304,185 | 4/1994 | Taylor | 606/147 |

*Primary Examiner*—Gary Jackson
*Attorney, Agent, or Firm*—Paul A. Coletti

[57] ABSTRACT

The invention described herein is a device for tying knots intracorporeally during laparoscopic surgery. It is intended to simplify the process of tying intracorporeal knots to the point that the average laparoscopist can quickly learn to suture laparoscopically with confidence. The unique features of this invention include: a driven shuttle; integral grasper or needle driver; the system is reloadable; and the system may have a detachable end effector. The system also may have a multi function handle, and incorporates an integral needle driver mechanism.

8 Claims, 19 Drawing Sheets

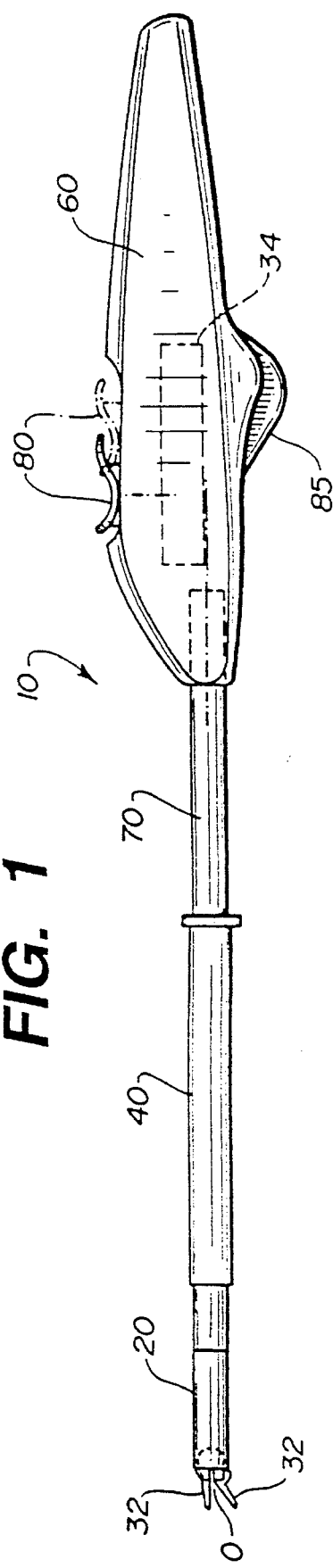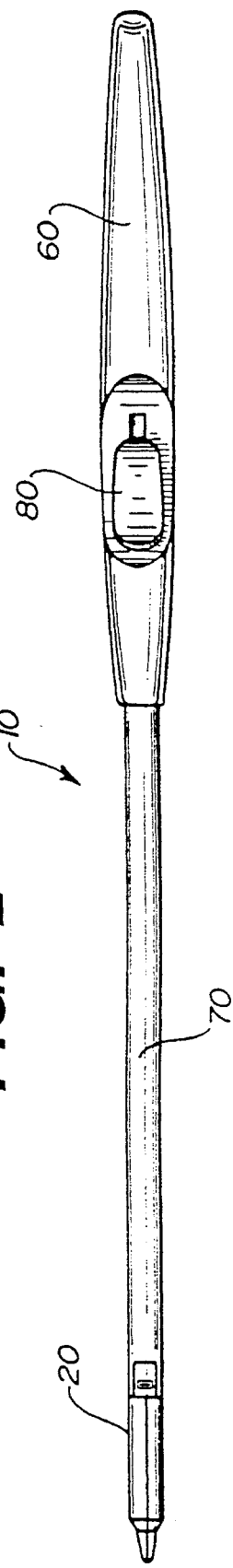

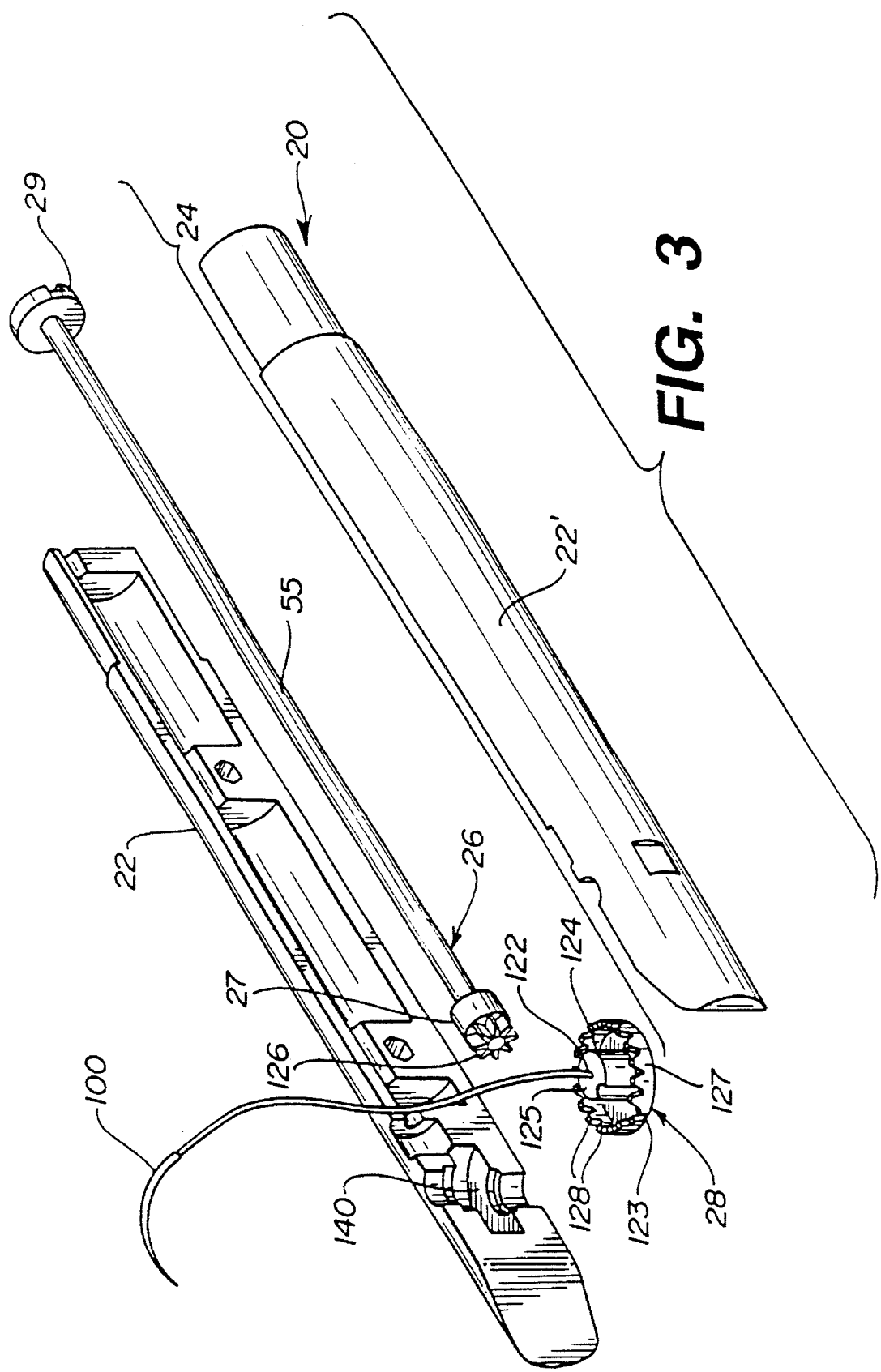

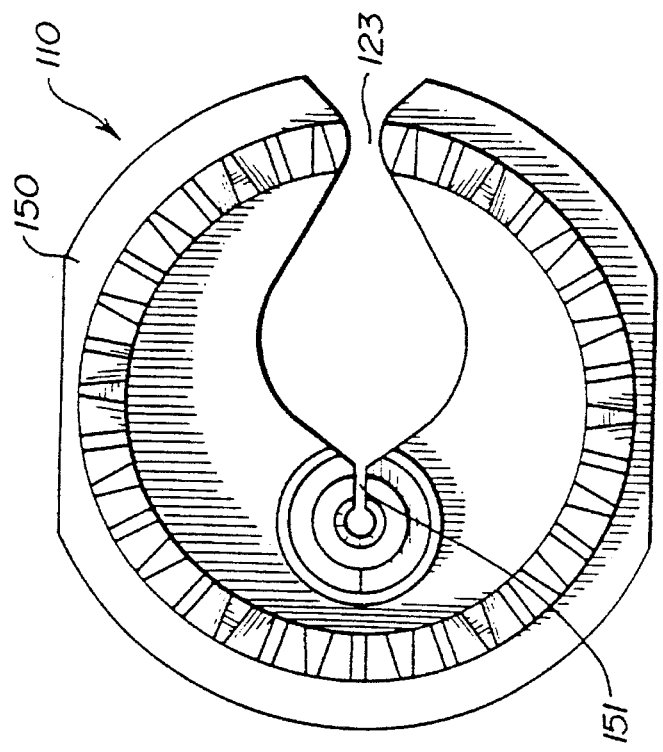
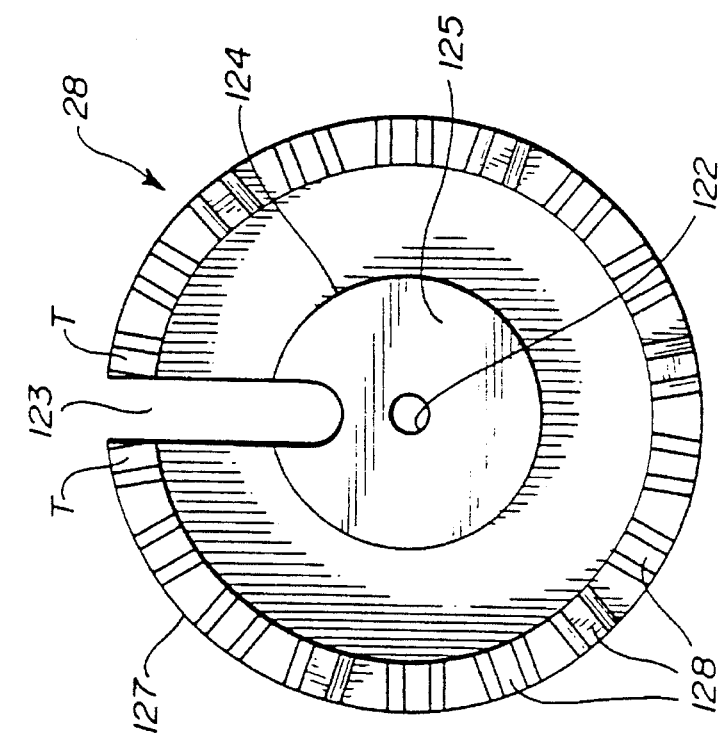
FIG. 14a
FIG. 14

NEEDLE DRIVING DEVICE

RELATED APPLICATION

This application is a continuation-in-part of Ser. No. 300,295, filed Sep. 2, 1994 pending entitled "Suturing Device", incorporated herein by reference.

BACKGROUND OF THE INVENTION

For surgeons, suturing was long the standard in tissue fastening and repair. But, with the advent of laparoscopic surgery, surgeons were removed from the immediacy of contact with the surgical site that aided suturing. The complicating aspects of laparoscopic suturing are the handling of the needle, the accurate placement of a stitch and the tying of a knot in the laparoscopic environment. The current techniques are complicated, take many hours to master, and are easily forgotten. As a result, many surgeons avoid laparoscopic suturing, preferring instead to either use alternate tissue fastening methods (clips, staples, endo-loops or loop-sutures), or to avoid those laparoscopic procedures which could require suturing.

SUMMARY OF THE INVENTION

The invention described herein is a device which integrates needle handling and knot tying intracorporeally during laparoscopic surgery such as those required for urinary stress incontinence (Birch) and gastric anti-reflux procedures (Nissen). It is intended to simplify the process of intracorporeal suturing to the point that the average laparoscopist can quickly learn to suture laparoscopically with confidence. It is an improvement on the design for a similar system, developed by Dr. Konstantin Zauza, U.S. Ser. No. 143,006 (END 67), incorporated herein by reference.

The unique features of this invention include:

A driven shuttle: The shuttle, the key component in creating the knot, is driven by a mechanism which is activated by the user. This embodiment takes the form of a face gear and pinion, but any mechanism which converts either linear or rotational motion into rotation along a different axis, and causes either one or more overhand throws to be formed in a suture like material, can be used.

Integral grasper: A grasper is included in this invention for the purpose of holding tissue or to position a needle and place a stitch.

The system is reloadable: This feature allows the system to be reloaded either with a suture designed to be used specifically with this device, or with a standard suture which has been modified by the user. The modification of the standard suture can be accomplished by the user at the time of use.

The device can be either a single patient disposable unit, or a system with a reusable handle and a detachable end effector designed to be single patient use and disposable. This ensures that the key functional components are new and reliable, and that the system is easy to clean.

For laparoscopic suturing, it is necessary to maintain control over the needle during stitch placement. Three types of motion must be resisted in suturing, these are: 1) rotation, or motion where the point and swage of the needle rotate in unison about the holding point; 2) toggle, or motion where the point and swage move in opposite directions about the holding point, but in the same plane; 3) slip, or motion where the needle slides in the holder, resulting in the holding point moving closer to the tip of the needle. Another requirement for needle holding is that it is easy to position the needle in the driver in a orientation suitable for placing a stitch.

This invention depicts a method which accomplishes the above tasks by using a gripping system comprised of three discrete contact points. This system uses the curvature of the needle to provide for a counter moment to rotation by supporting the needle along two points placed at a distance to each other, and by clamping with a third point between the first two. The curvature of the needle causes the center point to be at a different elevation than the support, thereby creating a moment which resists rotation. Resistance to toggling and slippage is provided by the clamping force of the grasper. The advantage of this invention over previous grasper designs is that the three point grasper will cause the needle to snap to a position wherein the plane of the curvature of the needle is vertical and perpendicular to the longitudinal axis of the instrument. This process is referred to as "righting" the needle.

DETAILED DESCRIPTION OF THE DRAWINGS

The invention described herein is better understood in conjunction with the following drawings, in which:

FIG. 1 is a side view of the instrument;

FIG. 2 is a top view of the instrument;

FIG. 3 is an exploded view of the distal end of the instrument;

FIG. 14 and 14a are views of the rotatable shuttle;

FIG. 16a is an exploded view of FIG. 16;

Figures 17, 17A:
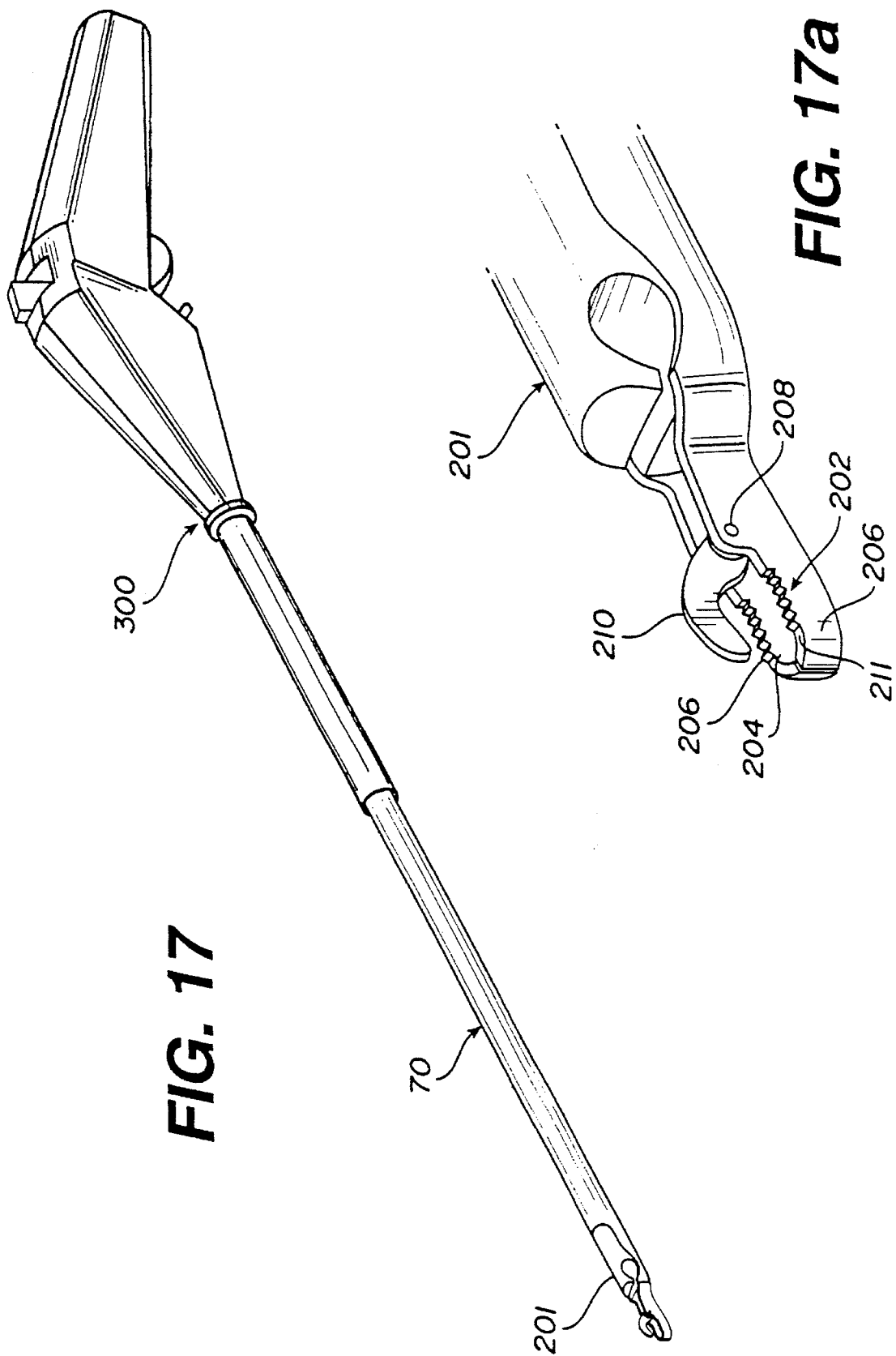

FIG. 17 discloses a alternative embodiment of the instrument with a needle grasping end effector, in perspective view with the needle grasping mechanism;

FIG. 17a is an enlarged view of the end effector.

Figure 18:
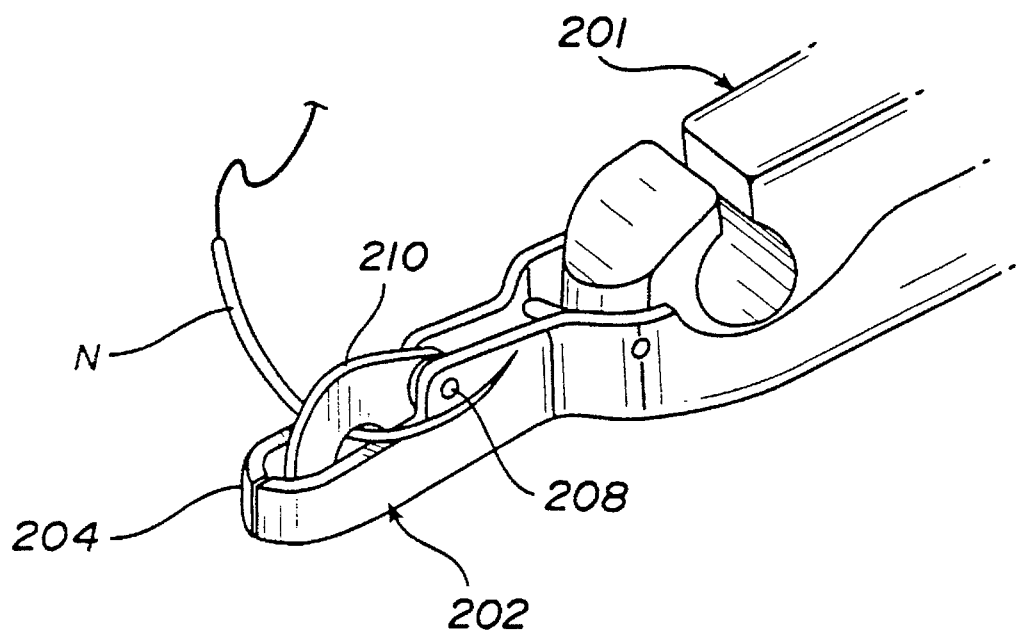
Figure 18A:
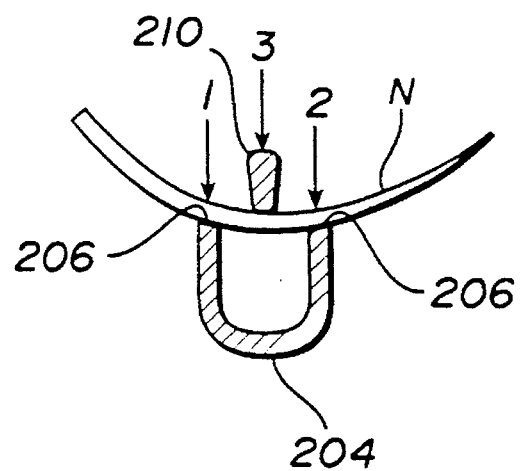
Figure 19:
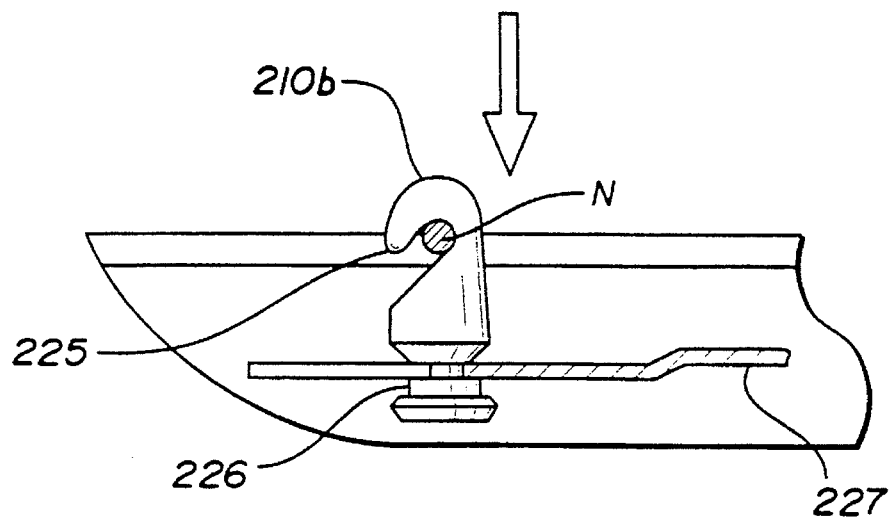
Figure 20:
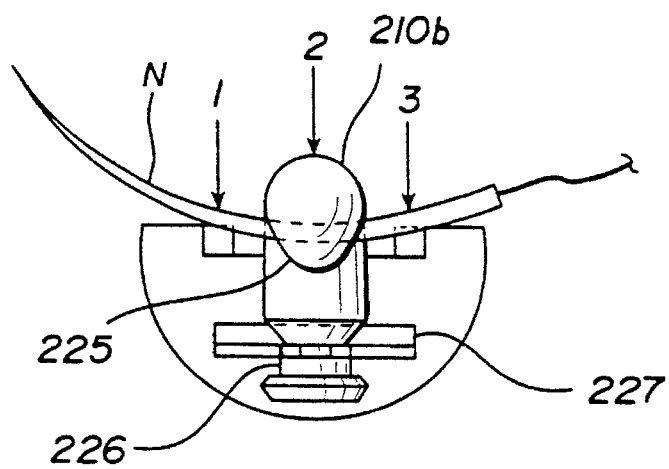
Figure 21:
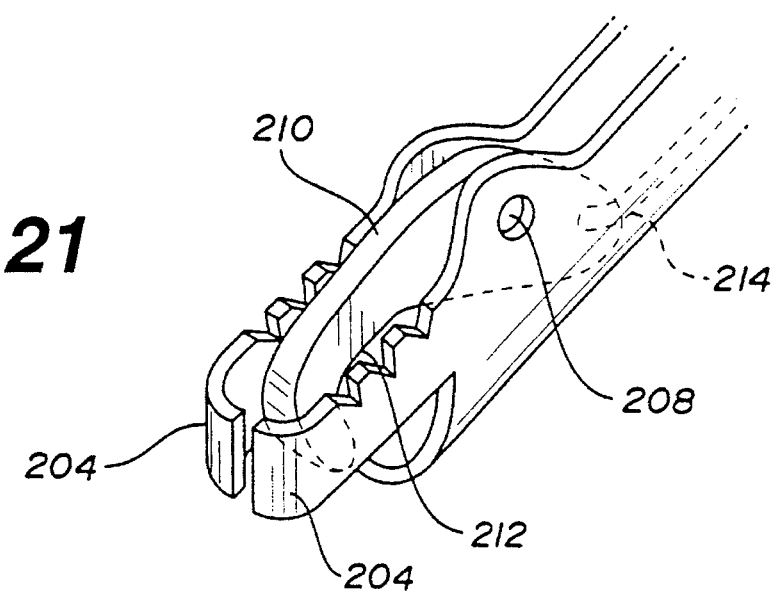
Figure 22:
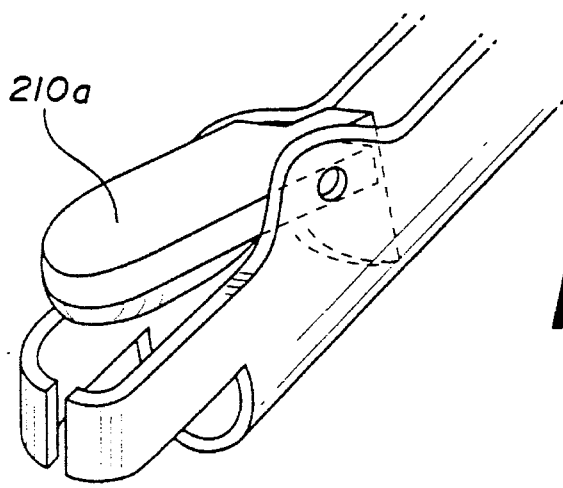
Figure 23:
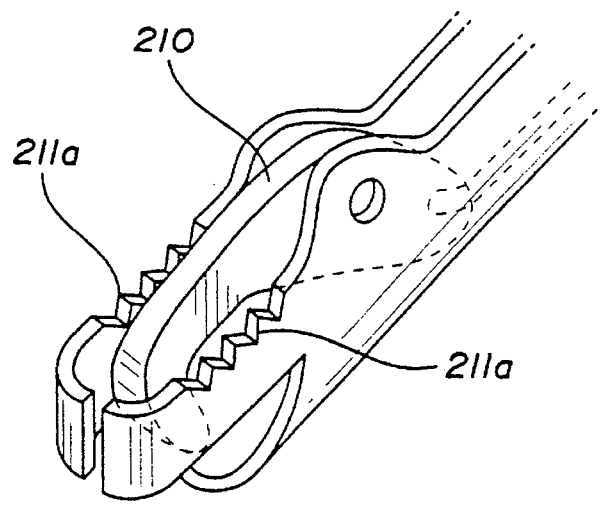

FIG. 18 describes a needle firmly locked in the end effector of FIG. 17;

FIG. 18a is a section view of needle locked in end effector showing the 3 point grasping system;

FIG. 19 describes yet another embodiment of the needle holding end effector;

FIG. 20 describes the effector of FIG. 19 in the locked position;

FIG. 21, 22 and 23 are perspective views of the instrument in use; and

Figure 24:
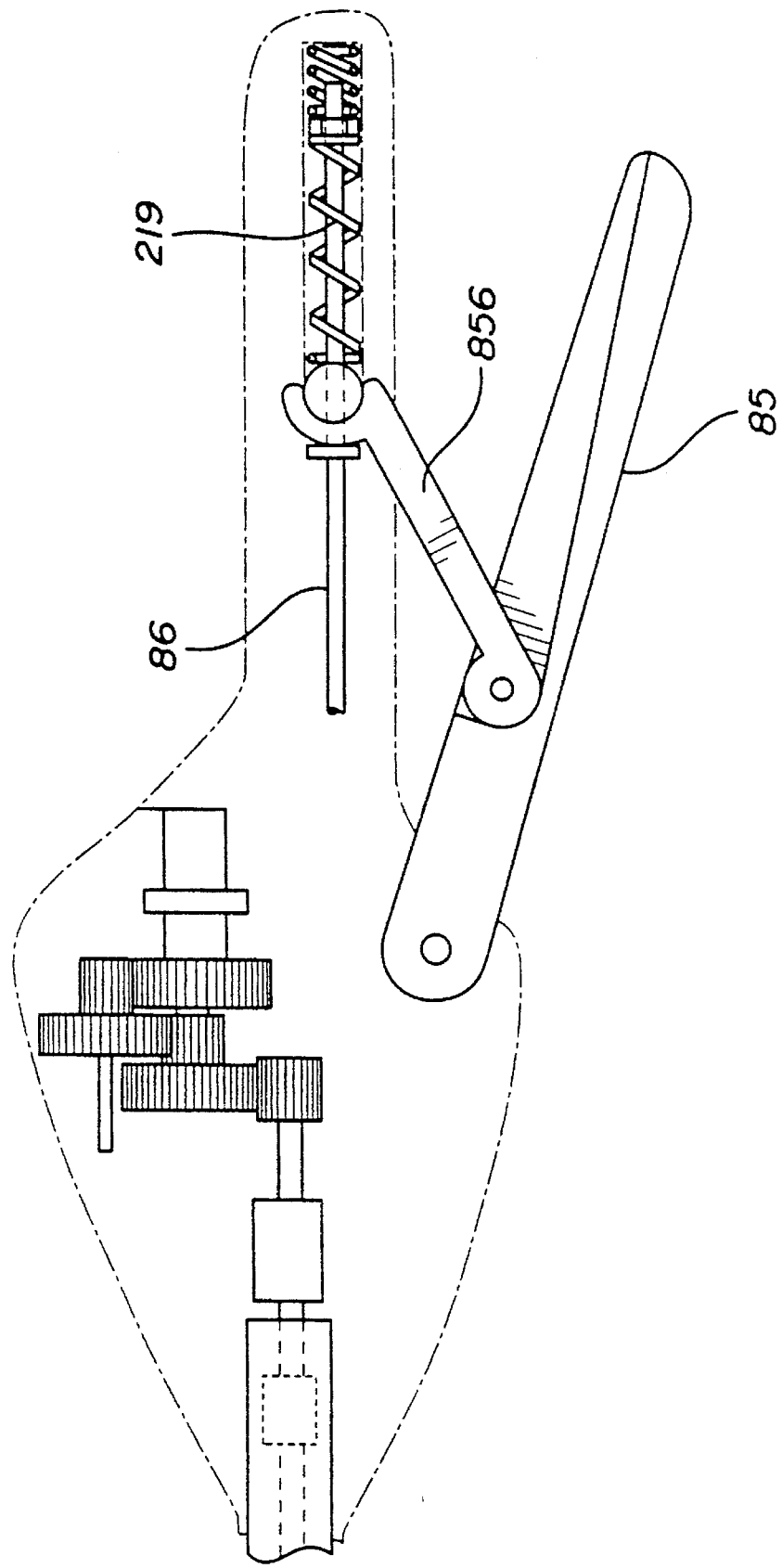

FIG. 24 is a section view of the handle of the instrument.

DETAILED DESCRIPTION OF THE INVENTION

Figure 16:
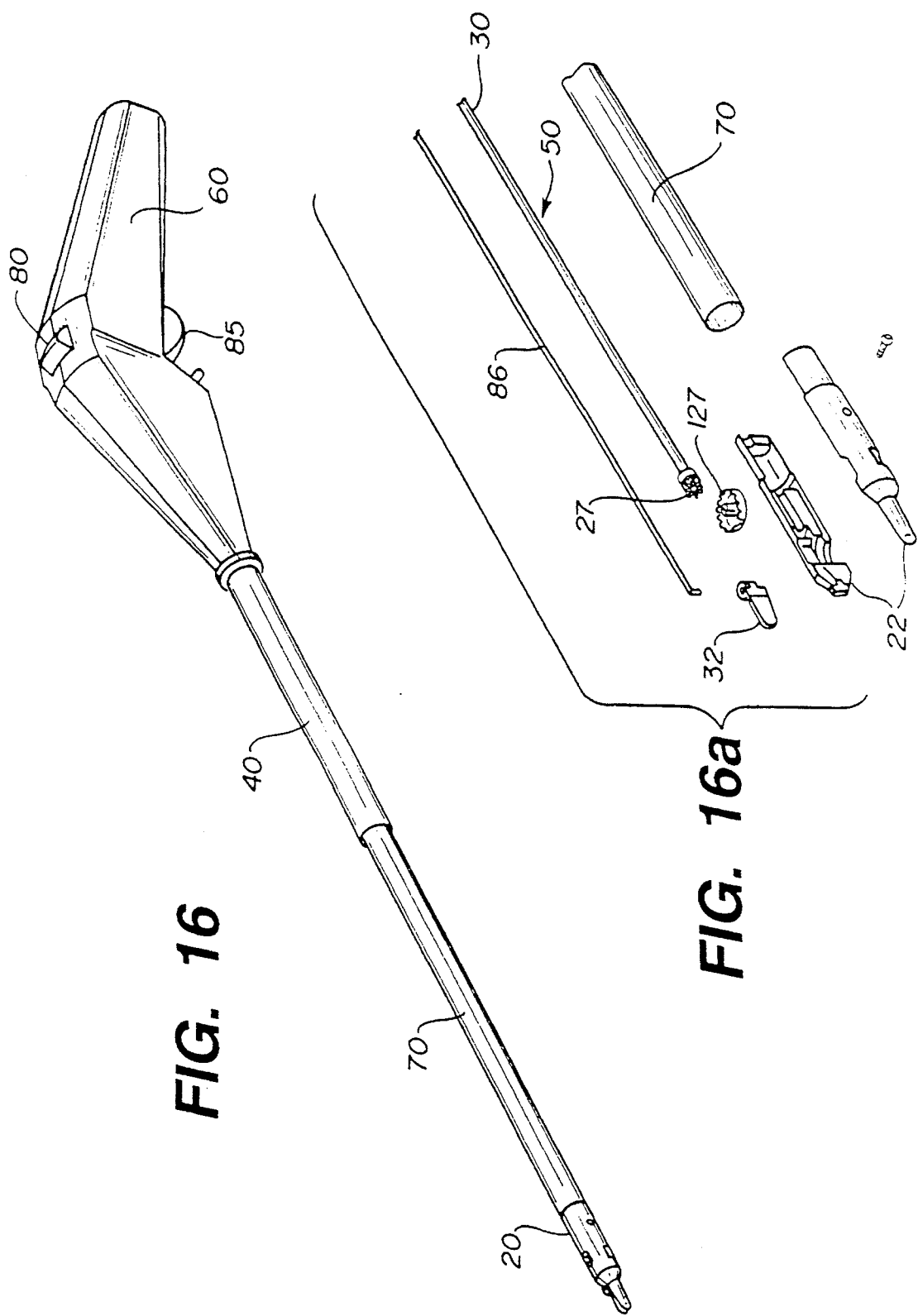
FIG. 16 is yet another alternate embodiment.

The device described herein can be produced in two configurations. One configuration would consist of an applicator 10 and a detachable end effector 20. This configuration would primarily be used when the applicator 10 is reusable. The end effector 20, which would be subject to becoming contaminated and wearing out, would be a single patient use disposable item. The second configuration (FIG. 16), one in which the end effector 20 and applicator 10 are integral, would be used for a single patient use disposable device.

Figure 11:
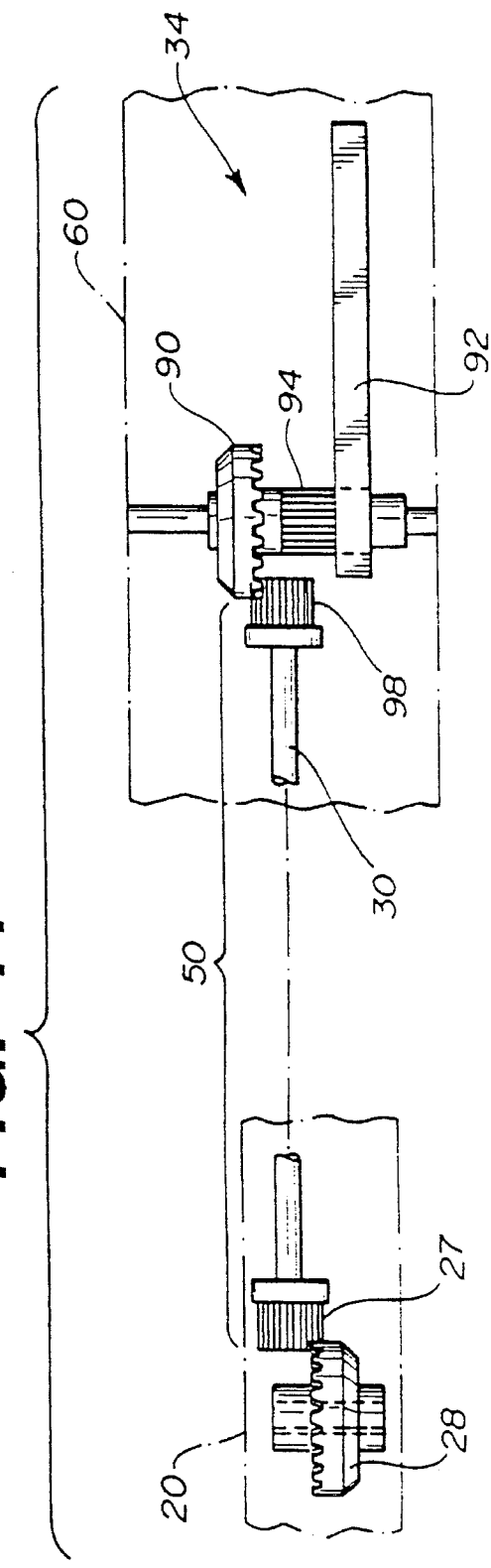
FIG. 11 is an exploded view of a gear driving mechanism.

When provided as a separate component, the end effector consists of the following sub-systems: 1) A two piece shell or cartridge 22 to hold the mechanisms, and to provide attachment to the applicator 10; 2) The knot tying mechanism 24 forming a drive mechanism consisting of a drive pinion assembly 26 and a shuttle gear 28 forming an alignment means; 3) A grasping system 30 (FIG. 1) consisting of a movable grasper jaw 32 (FIG. 1) and an actuation mechanism 85; and 4) A needle introduction or containment means 40 which will hold the surgical needle in such a position to allow easy introduction into the body cavity and to allow the needle 100 to be easily grasped by a secondary needle driver. These same sub-systems are included in the integral system, except that end effector 20 is permanently attached to the applicator 10 and the drive pinion assembly 26 is replaced by the main drive shaft 50 (FIG. 11).

Figure 10:
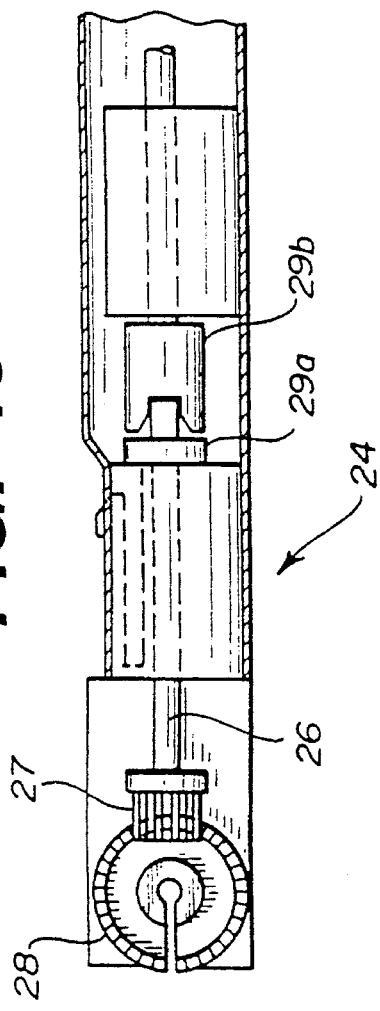
FIG. 10 is a cut away view of a detachable cartridge and drive connection.

The drive pinion assembly 26 consists of a pinion gear 27 and a drive shaft 55. The shaft 55 has a coupling means 29a, 29b (FIG. 10) on the proximal end for mating-with the applicator 10 in the two piece system. In the single piece system, the drive shaft 30 extends to the applicator handle 60 which contains the actuation mechanism 34.

The shuttle gear 28 (FIG. 14) is a modified right angle face gear 127. The teeth 128 of the face gear 127 are designed to mesh with the teeth 126 of the drive pinion 27. The hub region 125 of the face gear 127 consists of a cylinder 124 upon which the face gear 127 is asymmetrically mounted. A radial notch 123 is cut from the shuttle gear 28, passing between two teeth T on the face gear 127 and into the hub 125 of the assembly 28. This notch 123 may be rectangular in cross section, or it may open into a circular opening within the hub section. A hole 122, offset slightly from the centerline, protrudes through the hub 125 of the face gear 127, parallel to the long axis of the rotatable shuttle. The hole is located diametrically opposite to the above-described notch 123. The hole could be provided with a counter bore on one or both ends of the hole. The hole is sized to accept a surgical sutures, but is too small to pass a ferrule or knot tied on that suture. A counter bore is sized to accept a knot or ferrule on the end of the suture and is deep enough to allow the knot or ferrule to be completely recessed in the counter bore. (Another embodiment would to remove the center hub of the face gear. In this embodiment, support and guidance for the shuttle gear 110 (FIG. 14a) will be provided by a ridge or groove 150 located on the circumference of the shuttle gear.)

Figure 4:
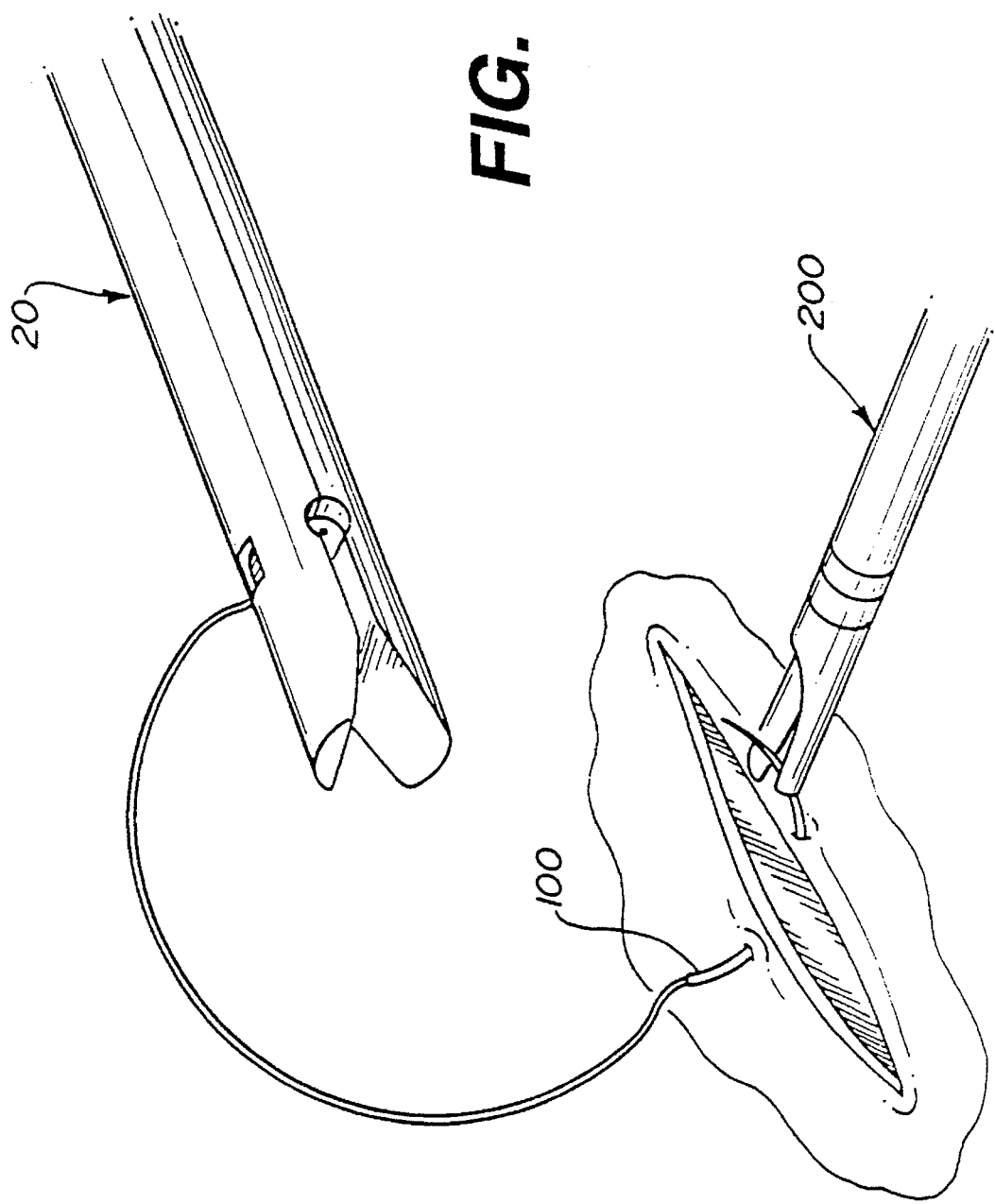
FIGS. 4 through 9 are step sequence views of use of the instrument of this invention.
Figure 5:
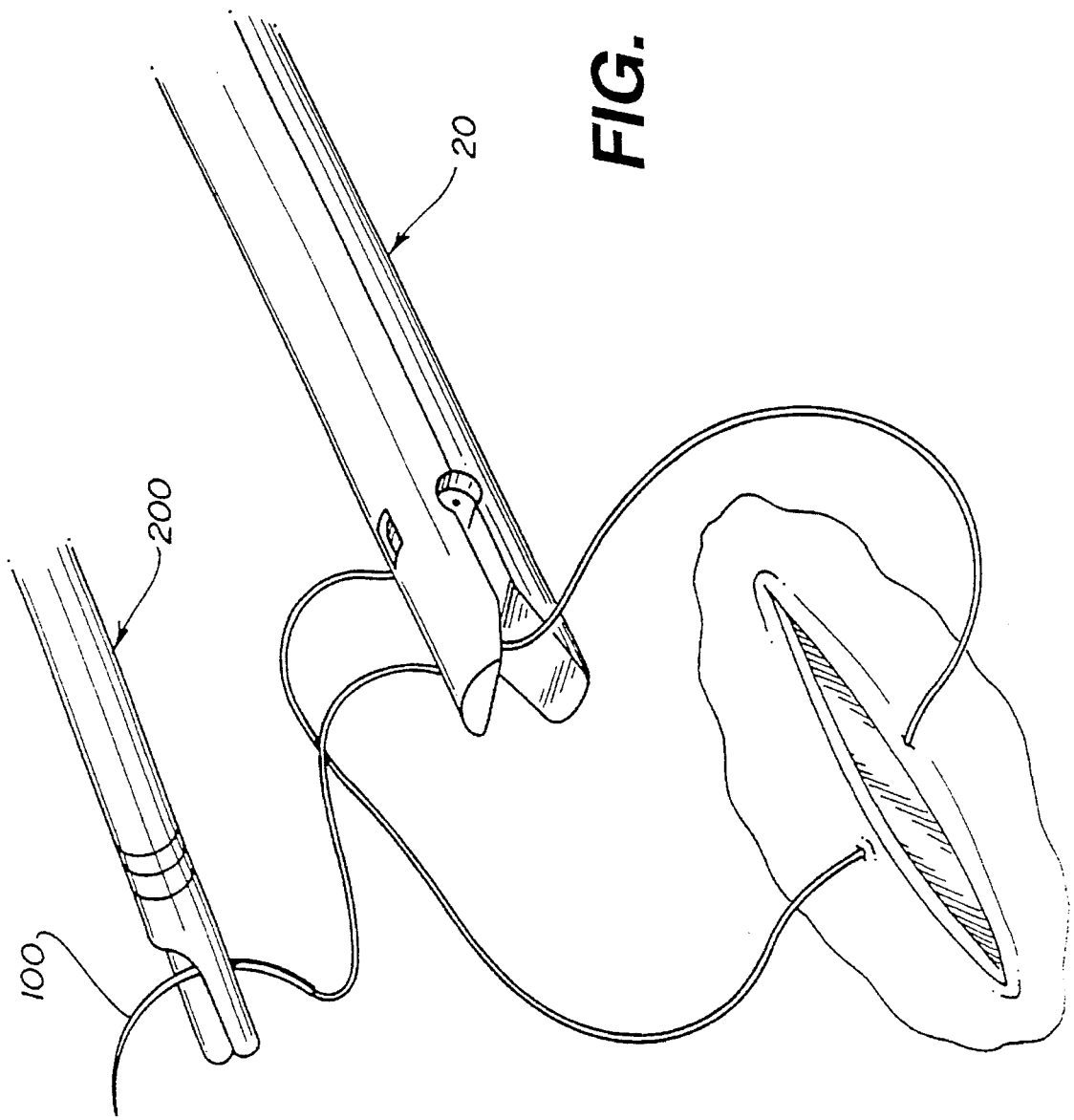
Figure 6:
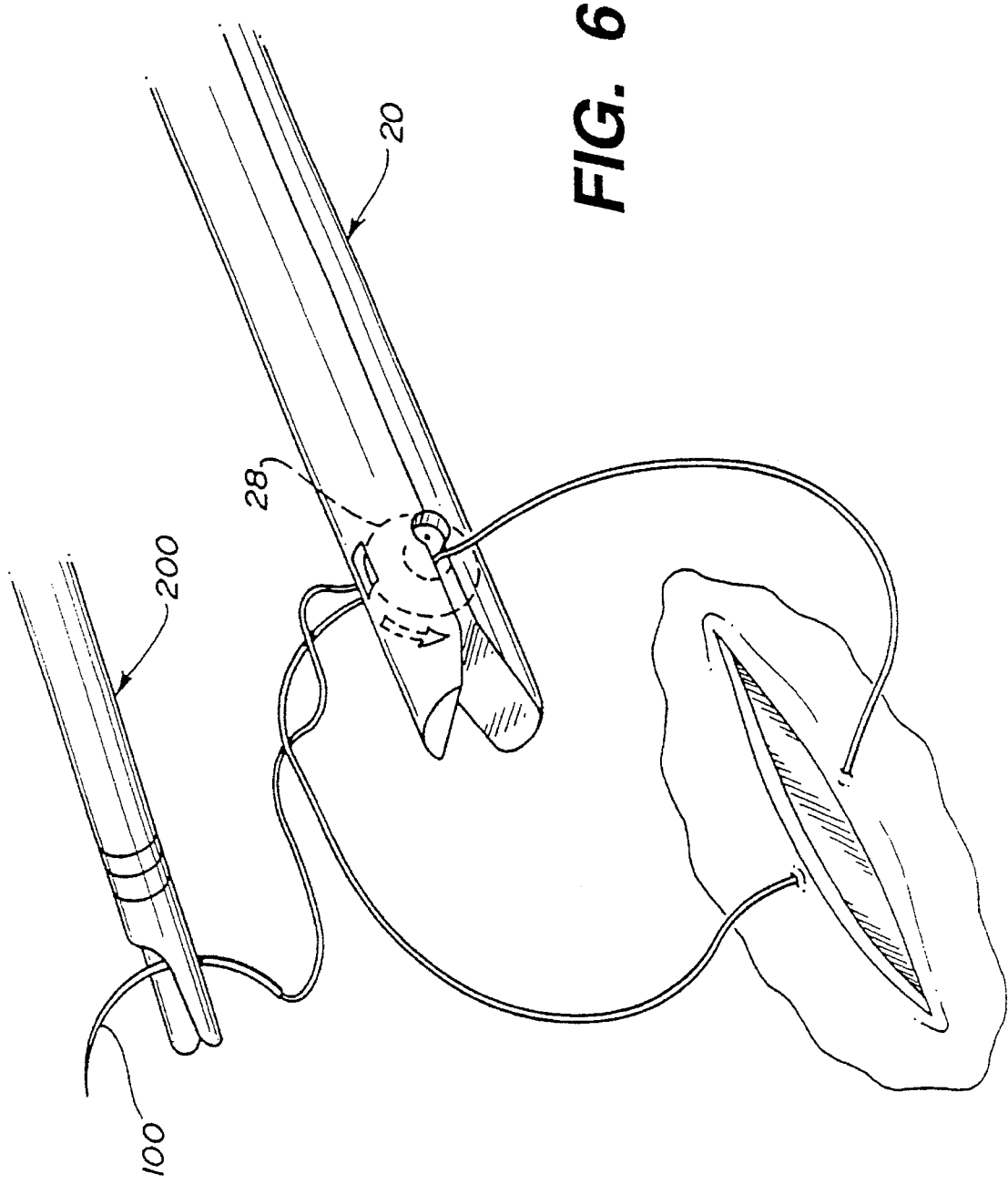
Figure 7:
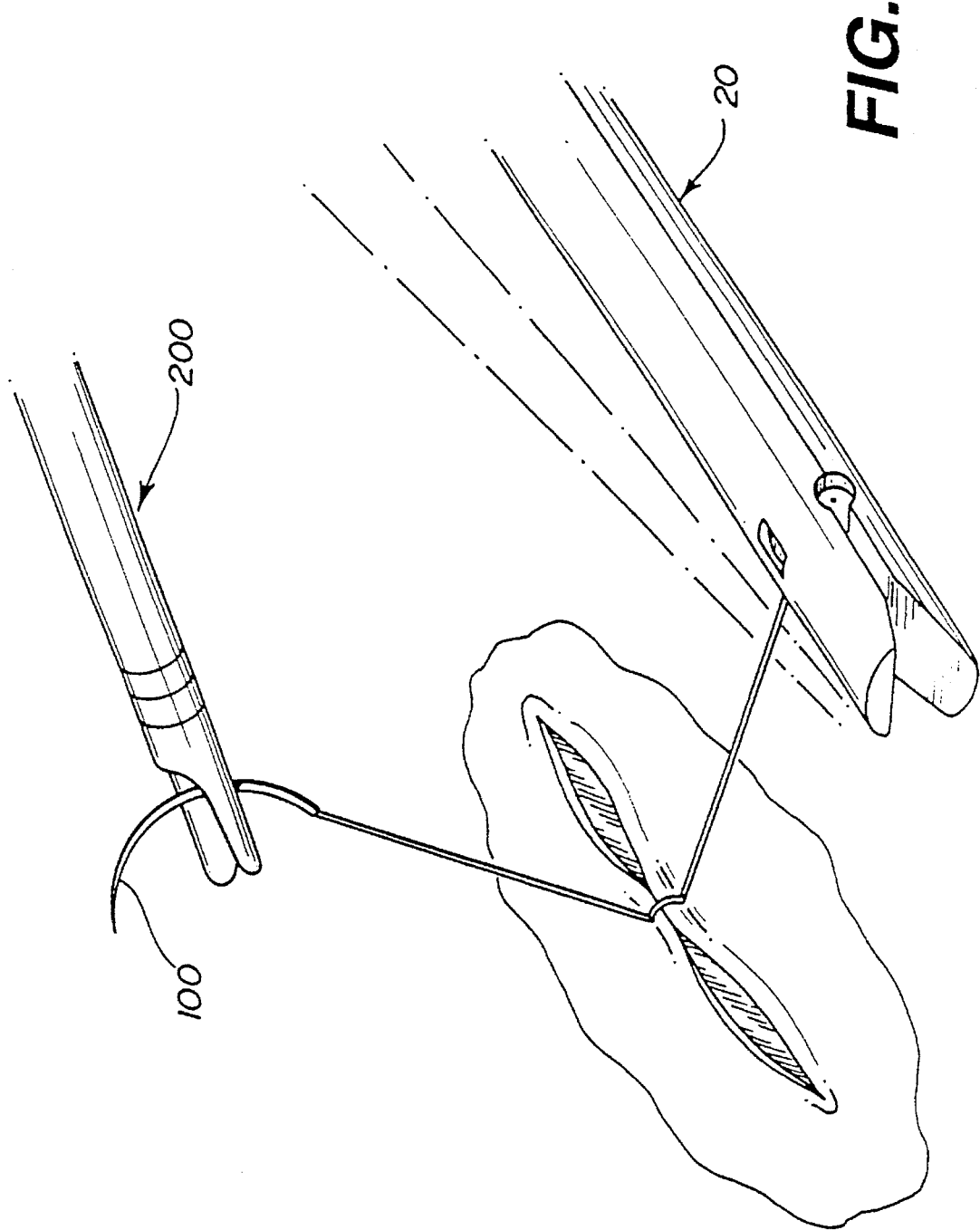
Figure 8:
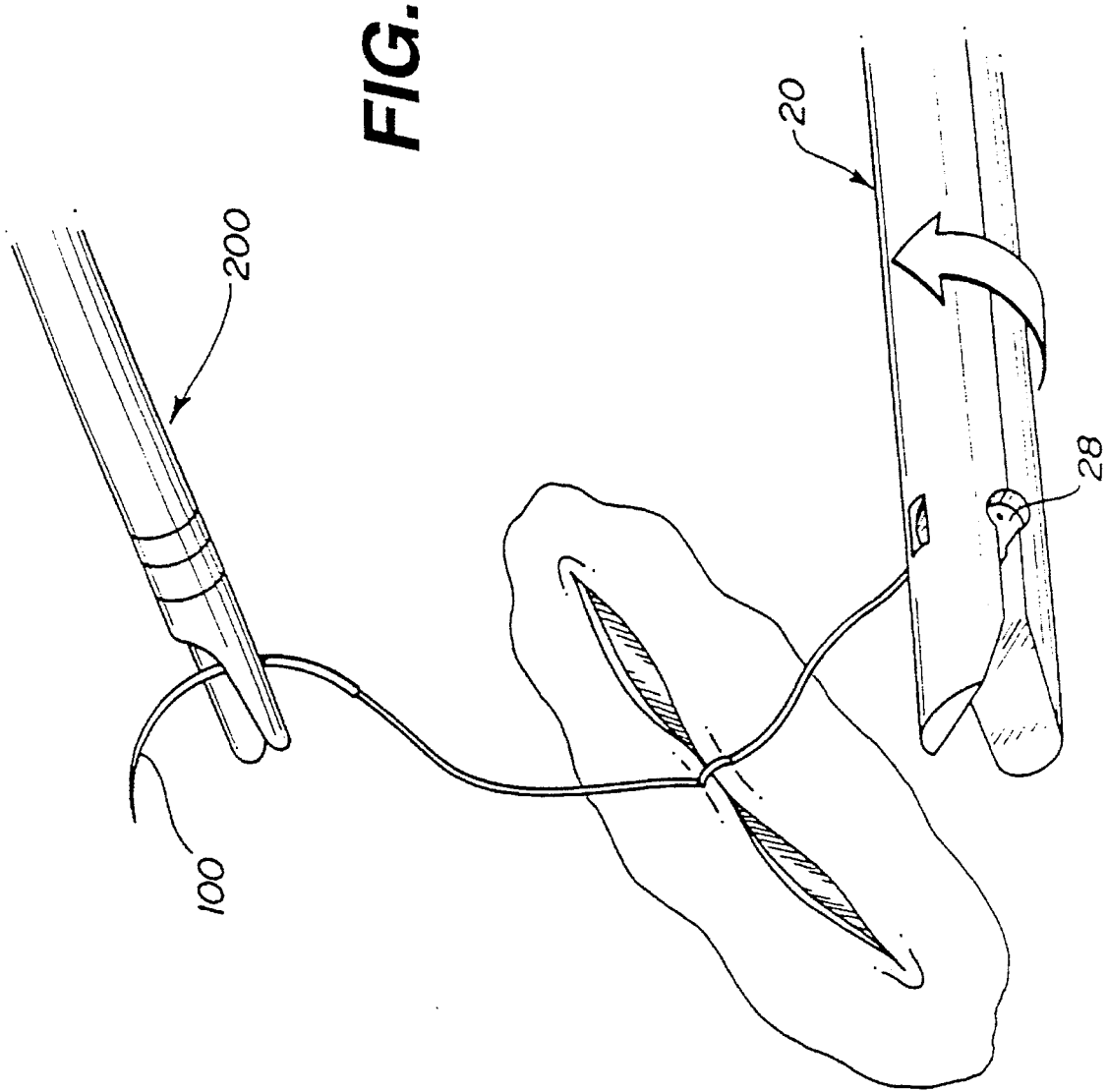
Figure 9:
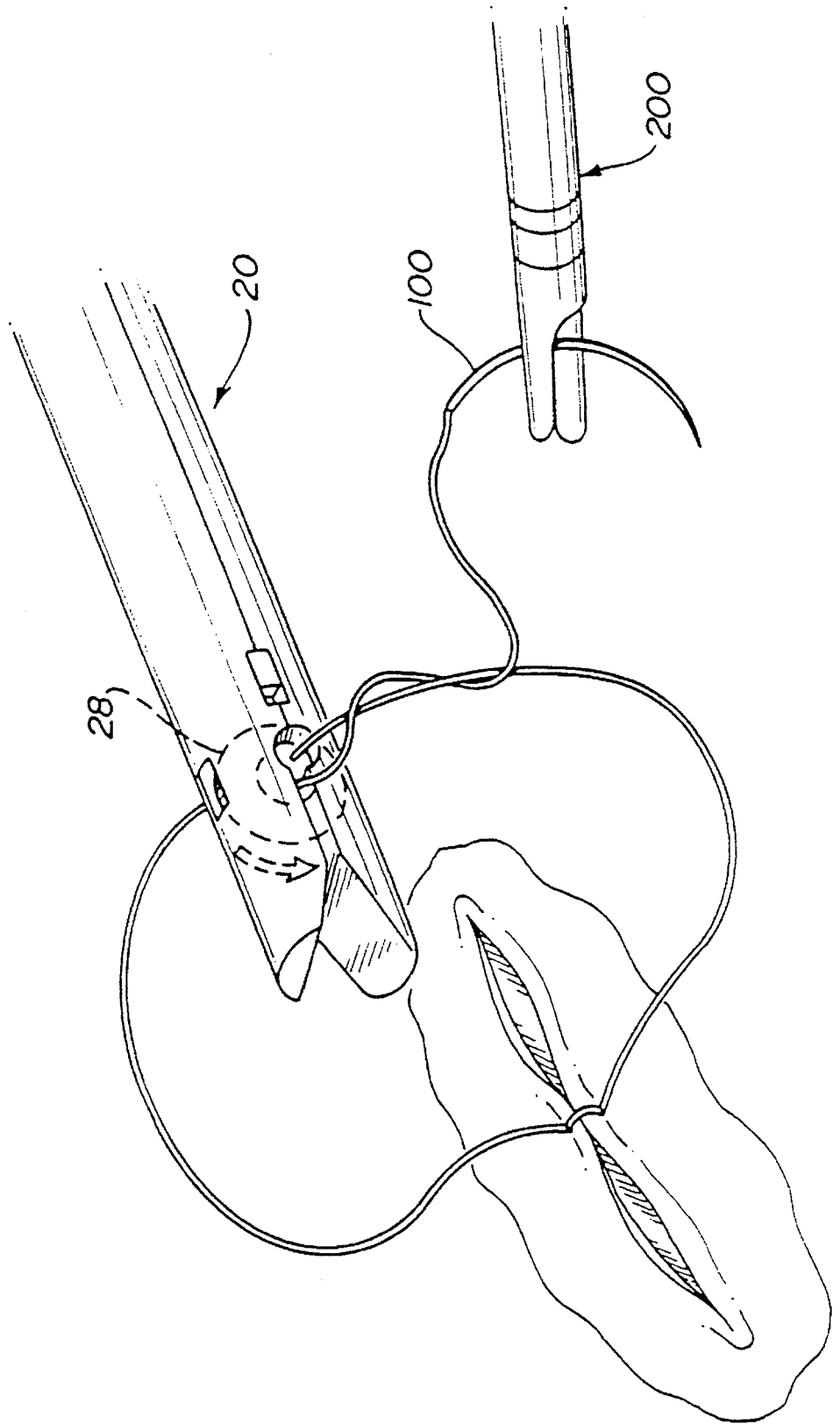

A shuttle gear assembly is created by attaching the free end of a short length of suture, attached to a surgical needle 100, to the shuttle gear 28. The free end of the suture is passed through the hole in the shuttle gear hub. A knot is tied on the free end of the suture, which in turn is pulled back into the counter bore. This locks the sutures to the shuttle gear 28. A small amount of adhesive may be placed in the counter bore to lock the suture in place. (An alternate method of assembly would be to provide a commutation 151 (FIG. 14a) between the aforementioned radial slot and the suture hole. In this embodiment, the suture assembly (FIG. 4), consisting of a short length of suture 160 with a surgical needle 100 on one end and a small ferrule 161 or knot on the other, is first placed into the radial slot 151 (FIG. 14a), pulled toward the end of that slot through the commutation means, and locked into the suture hole by pulling the knot or bead located on the free end of the suture into the counter bore. This would allow for reloading the instrument during a procedure, and would allow for standard sutures to be modified by the surgical staff to be used with the instrument.)

The cartridge 20 is a cylinder approximately one to one and a half inches long, and approximately ⅜" in diameter. The cartridge 20 is formed from a two-piece shell 22, 22'. The assembly is cavitated to accept the drive pinion 27 and shuttle gear 28. The cartridge 20 holds these parts in alignment, with the teeth of the drive pinion 27 engaged with the teeth on the shuttle gear assembly 28. Both the shuttle gear assembly and drive pinion assembly are allowed to rotate along their respective long axe. The drive pinion gear assembly 26 is positioned parallel to the long axis of the cartridge 20. The shuttle gear 28 is positioned perpendicular to the long axis of the cartridge 20 and is closer to the distal end of the cartridge assembly.

An opening O is provided near the distal end of the cartridge 20 which will allow a length of sutures to be placed into the aforementioned radial notch 123 in the shuttle gear 28. This opening O will be "V" shaped to facilitate the introduction of the sutures. This opening terminates into a series of concentric cylindrical cavitations 140, all positioned perpendicular to the long axis of the cartridge 20 and parallel and co-planar to the parting line plane. These cylinders are sized to accept the shuttle gear 28 and to allow for its free rotation. The innermost cavitation 140 (FIG. 3) extends through the cartridge 20, forming a lip on the outer wall of the cylinder which will retain the shuttle gear 28 along its long axis. The shuttle gear is positioned in the cavitations in the cartridge so that its radial notch 123 extends into the apex of the cartridge "V" slot O describing a lead into the shuttle gear notch.

When the cartridge assembly is complete, the shuttle gear 28 can be rotated by rotating the drive pinion gear assembly 26. The notch 123 in the shuttle gear 28 will line up with the notch O near the distal end of the cartridge 20 once for each revolution of the shuttle gear. The "home" position for the assembly is when the slot O in the cartridge 20 and shuttle gear notch 123 are in alignment.

The applicator 10 consists of a cannula 70, handle assembly 60, an activator for tying knots 80, an activator 85 for the grasper and, internal to the handle 60, the drive mechanism 34 for the drive shaft assembly 50.

Figure 12:
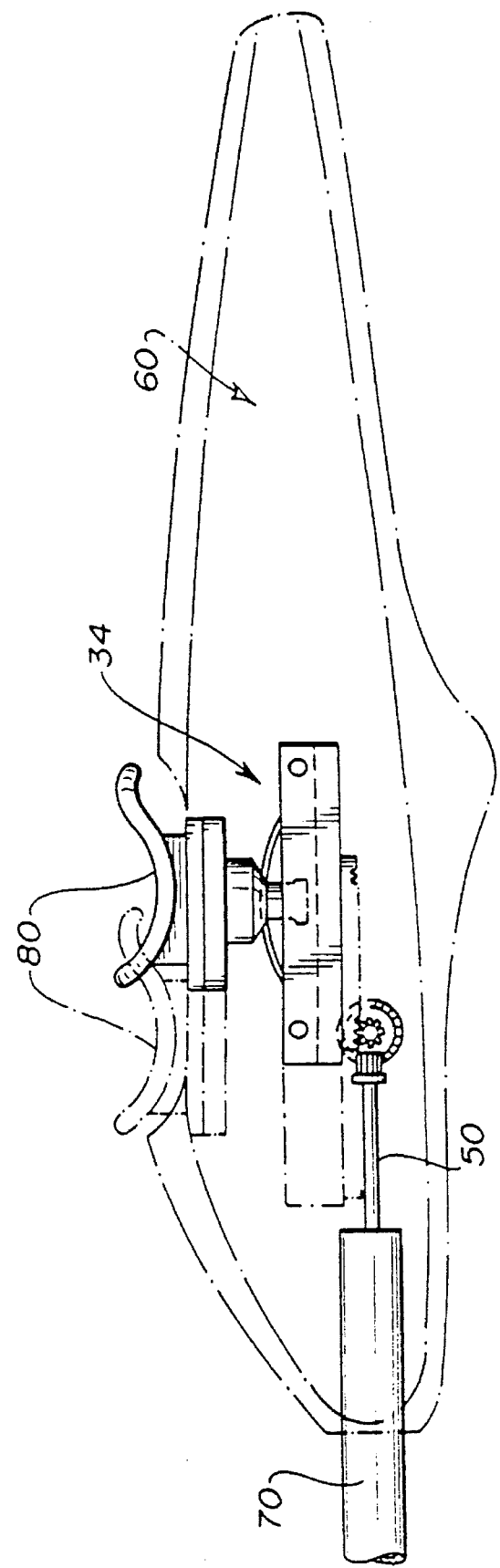
FIG. 12 is a view of the handle assembly, showing both positions of the actuator.
Figure 15:
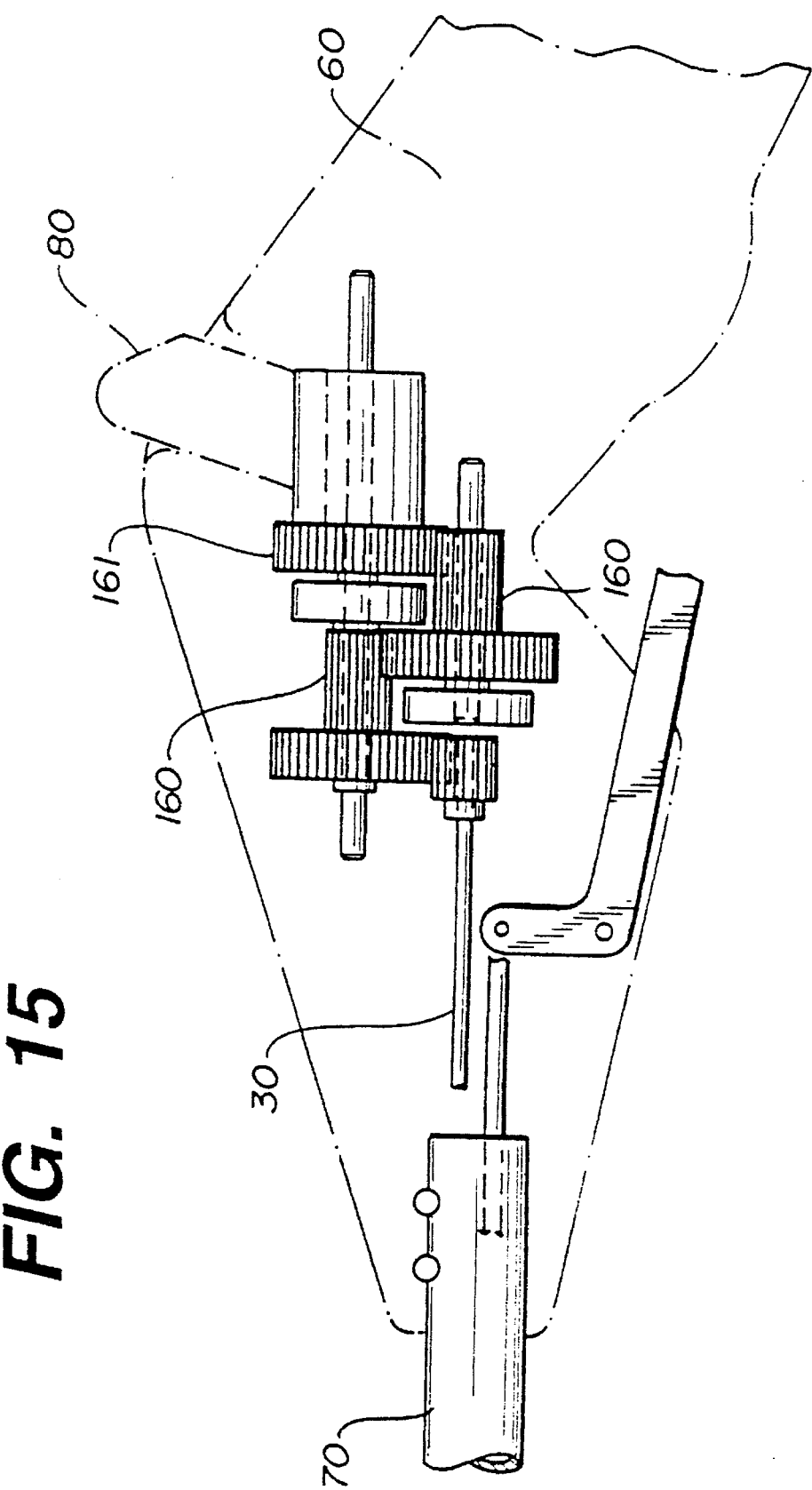
FIG. 15 is an alternate gear mechanism.

The drive mechanism assembly 34 (FIG. 11 & 12) consists of a sliding rack gear 92 engaged to a first pinion gear 94, a face gear 90 joined to the same shaft as the first pinion gear 94, and another pinion 98 which is attached to the main drive shaft 30, positioned at right angles and engaged with the face gear 90. When the slide rack 92 is moved distally or proximally and parallel to the long axis of the handle 60, the engaged pinion is caused to rotate. This, in turn, causes the face gear 90 to turn which causes the pinion 98 on the main drive shaft 30 to turn. The end result is that the shuttle gear 28 turns a specific number of turns for a given linear motion of the slide rack 92. Motion of the slide rack 92 can be caused by either direct input, from the user, or through a secondary mechanism. An alternate means would be to provide a series of intermeshing stepped spur gears 160 (FIG. 15). Here a small arc-like motion of the input gear 161 would result in multiple revolutions of the drive shaft 30. The drive mechanism could be any mechanism which will convert an input motion from the user into the required motion to activate the driven shuttle. The grasper activator 85 (FIG. 13) connects to the grasper jaws 32 (FIG. 1 ) via a linkage 86, 87 (FIG. 13) that converts an input motion from the user into a linear motion of the grasper link 86. Linear movement of this link causes the grasper jaws 32 to move into approximation.

The applicator cannula 70 provides a means to seal against the trocar used to introduce the device into the body cavity, to provide a support for the drive shaft 30 and the grasper linkage 86, and to provide a coupling means for the cartridge assembly 20 when not an integral part of the instrument. The cannula 70 could also be part of the disposable portion of the configuration wherein the handle is reusable.

As seen in FIGS. 4 through 9, the device functions as follows:

1. If required an end effector is attached to an applicator assembly, a suture is loaded into the shuttle gear, and the needle is covered with the introducer. This assembly is then inserted into the body cavity through a trocar.
2. The needle attached to the suture in the assembly is picked up by a secondary needle holder 200, positioned to make a stitch, and is passed through the tissue.
3. The end effector assembly is positioned so that when the free end of the suture (the one with the needle) is brought into the "V" notch on the distal end of the cartridge, it is on the same side of the cartridge that the suture protrudes from the shuttle. The suture is drawn into this notch until it rests completely within the hub region of shuttle gear.
4. The applicator is then activated, causing the shuttle gear to rotate so that the notch turns into the loop created by the suture. One 360° revolution creates half of a square knot. If a 720° turn is made, half of a surgeon's knot is created.
5. The suture is removed from the cartridge and the ends are pulled apart, drawing the throw of the knot down to the tissue to the desired tightness.
6. The third through the fifth steps are repeated as many times as necessary to secure the knot, alternating direction of shuttle gear rotation for each throw, and tightening the knot between each throw.
7. When the knot is complete, the suture is cut. The needle is removed using the secondary needle holder. The cartridge is withdrawn and the suture is replaced if additional stitches are to be made.

The instrument incorporating a needle driver consists of the following elements, all of which are mounted distal to the knot tying mechanism 201 of the suturing device 300 (FIG. 17).

Jaw 202: The jaw 202 of the device is the distalmost portion of the instrument. It is a channel 204 with a "U" or "V" shaped cross section and can either be closed or open in the distalmost end. The vertical walls 206 of the jaw channel 204 form the two outer supports for the needle N. The channel in this invention is an extension of the instrument cannula 70 which has been necked down to provide improved access to the operative site. A hinge point 208 for the gripping member 210 (pawl) is located on the proximal end of the gripping region of this channel. The upper edge of the channel jaw 211 may be provided with serration or grooves 211 a, FIG. 23, which will assist in resisting toggle motion of pawl 210.

The pawl 210 (FIG. 21 ) is the movable portion of the needle driver and is the element which performs the actual clamping of the needle N. It is located between the outer walls of the jaw channel 204. It consists of a gripping surface 21 2, a hinge point 208, and a activation lever arm 214. This member 210 is hinged about an axis that is perpendicular to the longitudinal axis of the instrument at the aforementioned location on the jaw channel. The pawl 210 is activated by a linkage 86 (FIG. 13) attached to an activation lever arm 87 (FIG. 13) which in turn is attached to a closing trigger 85 (FIG. 13) located in the instrument handle. There are three possible embodiments for the pawl 210.

In the first embodiment, the pawl is a thin member spaced in the center of the channel jaw (FIG. 21 ). The contour of the gripping surface is designed so that when the jaw is open the surface is parallel to the channel jaw, and when closed the surface approximates a shallow "V" which holds the needle in a specific position in the grasper jaw, preventing the needle from "walking" during the suturing process. When the pawl is closed, it strikes the needle between the channel jaw supports thereby providing the three point gripping system (arrows 1, 2 and 3 of FIG. 18*a*).

The second embodiment is a more conventional design for a needle driver pawl with a broad gripping surface which spans the distance between the two outer edges of the channel jaw 210*a* (FIG. 22). The unique feature of this embodiment is that the gripping surface is crowned. The crowned surface of the jaw mimics the three point support system in that the crown contacts the needle first causing it to right itself and counteracting rotation of the needle. As the jaw continues to close the outer edges of the jaw clamp the needle to the channel jaw walls providing additional stability.

In the third embodiment, FIG. 19, the pawl 210*b* is in the form of a plunger rather than a hinged member. The pawl is mounted perpendicular to the longitudinal axis of the grasper, and between the jaw channel walls. The pawl has a hook 225 on the upper end for grasping the needle, and a guide pin or slot 226 on the lower end for engaging the cam activator 227. The pawl is activated by moving a cam activator parallel to the longitudinal axis of the instrument. This in turn causes the guide pin or slot in the pawl to trace the path in the activator cam, causing the pawl to move down. Continued movement of the cam activator places additional downward pressure on the pawl causing the needle to right itself, and to provide clamping action on the needle in a fashion similar to the three point gripping systems listed above (see FIG. 20).

Activator Rod 86 (FIG. 13): The activator rod provides a means to translate the closing action from the closing trigger 85 on the handle to the pawl 210. Specifically this device translates the linear motion and force created by the closing linkage to the activation lever or cam activator at the distal end of the instrument. This member could also be designed with a compliant member, such as a spring, which would limit the amount of force which could be transmitted to the pawl, and automatically adjust for assembly tolerances and size of needle grasped. This invention describes a linear motion activator, however of course the activator could translate any type of motion which could cause the pawl to close on the channel jaw.

Closing Trigger 85: This mechanism translates user input into useful mechanical motion and force for the type of pawl activator employed. The embodiments described herein describe two types of linkages.

Figure 13:
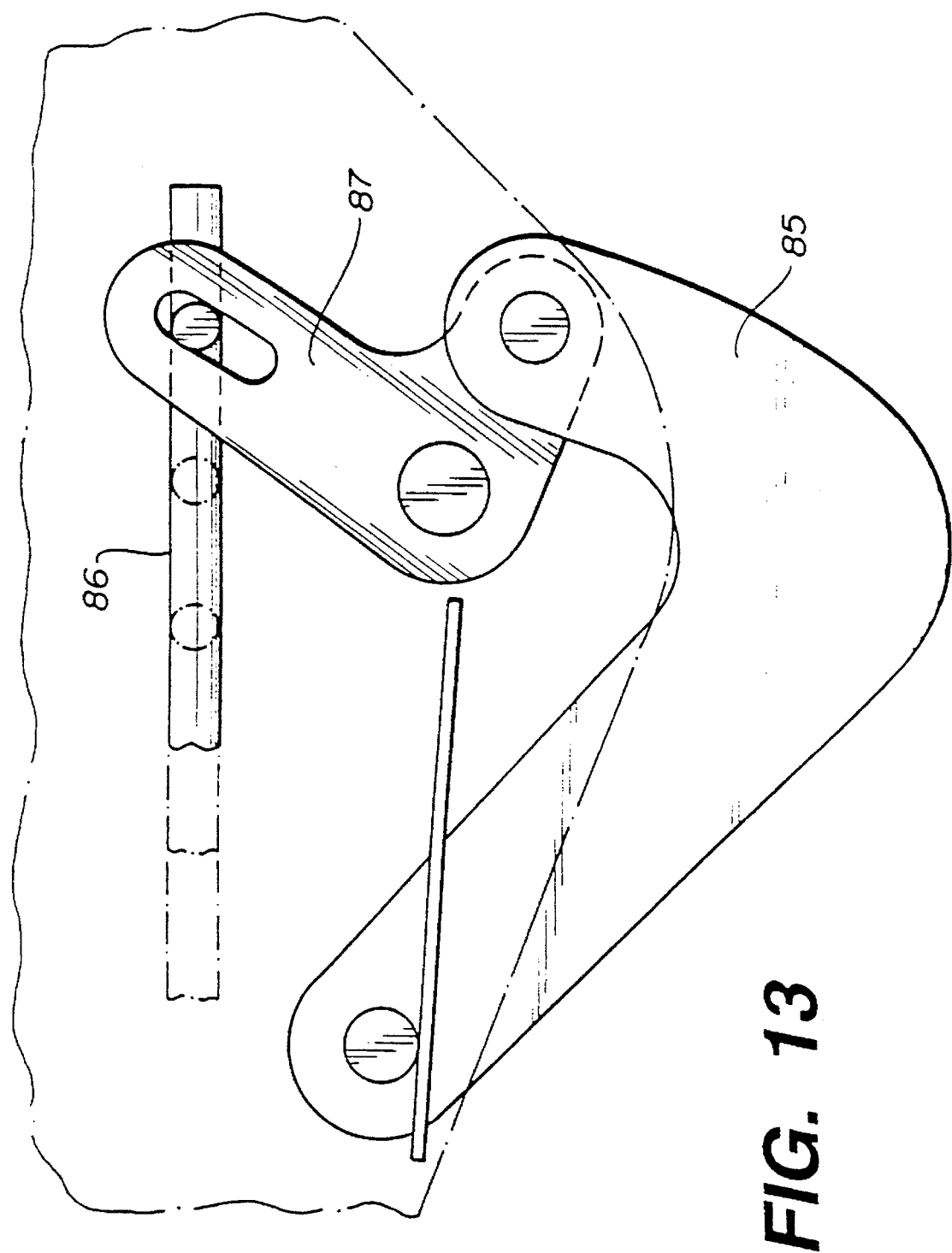
FIG. 13 is a view of an actuation linkage.

The first embodiment is a simple bell crank linkage (FIG. 13). Here the activator rod is connected to a "L" shaped link 87. This link is spring loaded to bias the needle grasping pawl close. By pulling on the trigger 85, the grasping pawl is caused to open for the purpose of either releasing or loading the needle. The same linkage could be employed, using a different hinge point, which would cause the grasping pawl to close when the trigger is pulled.

The second embodiment employs a toggle linkage (FIG. 24). Here, the activator rod 86 is attached to the movable end of a toggle linkage 856. When force and motion are applied to the apex of the toggle, the linkage flattens, causing the free end to move roughly perpendicular and away from the input motion. This in turn causes the activator rod 86 to move in such a fashion as to cause the grasping pawl 210 to close. This linkage could be provided with a compliant member 219, such as a spring, which could provide a means to ensure the mechanism does not overload the grasping pawl, and provide adjustment for assembly and different size needles.

What is claimed is:

1. In combination:

a curved surgical needle; and a surgical suture device comprising:

a shaft;

a rod extending through the shaft and movable therein;

a cartridge connected to said shaft;

a suture fixedly held on a rotatable suture wheel placed on said cartridge said suture wheel having a mechanism for mating with said rod and said cartridge having a proximal end attached to said shaft; and an actuating mechanism connected proximally to said shaft, said actuating mechanism operable to cause said rod to rotate said suture wheel;

a needle holder for endoscopically engaging said needle, said holder comprising:

a tubular endoscopic section ending in a distal, needle holding end effector lying along a longitudinal axis on said needle holder;

said end effector containing a groove for placing said needle transverse to the longitudinal axis of said end effector and a grasping finger located distal said groove, said finger capable of being emplaced over said needle when said needle is seated in said groove.

2. In combination:

a curved surgical needle; and a needle holder for endoscopically engaging said needle, said holder comprising:

a tubular endoscopic section ending in a distal, needle holding end effector lying along a longitudinal axis on said needle holder;

said end effector comprising a channel containing side walls parallel to the longitudinal axis of said needle holder thereby forming two supports for said curved needle, and a grasping finger located between said walls, said finger being capable of being emplaced over said needle forming a third support point thereby causing clamping of said needle therein and a resistance against rotation of said needle.

3. The combination of claim 2 wherein said finger has a gripping surface formed by at least one groove wherein said needle can be seated in a said groove.

4. The combination of claim 2 wherein said finger is actuable by a toggle mechanism connected to a proximal end of the endoscopic section and said finger connected to said toggle mechanism by means located on the said tubular endoscopic section.

5. The combination of claim 2 wherein said finger is actuable by a slide mechanism connected to a proximal end of the endoscopic section and said finger connected to said slide mechanism by means located on the said tubular endoscopic section.

6. The combination of claim 2 wherein the gripping surface of said finger has an inverted "V" shape which, when closed, draws the needle to a specific location on said channel.

7. The combination of claim 2 wherein the gripping surface is approximately the same width as said channel, and is crowned such that the center of said finger contacts the needle.

8. The combination of claim 2 wherein the finger comprises a plunger mounted between said channels.

* * * * *